US011402976B1

(12) United States Patent
Palamadai et al.

(10) Patent No.: US 11,402,976 B1
(45) Date of Patent: Aug. 2, 2022

(54) SYSTEM AND METHOD FOR AN ADAPTABLE, SMART VIRTUAL ASSISTANT THAT SUPPORTS LONG TERM CARE

(71) Applicant: AT&T Intellectual Property I, L.P., Atlanta, GA (US)

(72) Inventors: Rashmi Palamadai, Naperville, IL (US); Eric Zavesky, Austin, TX (US); Nigel Bradley, Canton, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 0 days.

(21) Appl. No.: 17/308,226

(22) Filed: May 5, 2021

(51) Int. Cl.
*G06F 3/0484* (2022.01)
(52) U.S. Cl.
CPC ................. *G06F 3/0484* (2013.01)
(58) Field of Classification Search
CPC ............... G06F 3/0484; G06F 3/048
See application file for complete search history.

(56) References Cited

U.S. PATENT DOCUMENTS

| | | | |
|---|---|---|---|
| 2,685,615 A | 8/1954 | Biddulph et al. | |
| 10,945,659 B1* | 3/2021 | Kahn | A61B 5/4812 |
| 11,094,180 B1* | 8/2021 | Williams | G16H 50/20 |
| 2016/0248865 A1* | 8/2016 | Dotan-Cohen | H04L 67/26 |
| 2018/0288063 A1* | 10/2018 | Koottayi | H04L 63/102 |
| 2019/0252079 A1* | 8/2019 | Constantin | A61B 5/7475 |
| 2020/0020447 A1* | 1/2020 | Generoso | G16H 50/70 |
| 2020/0098467 A1* | 3/2020 | Chakra | G06F 16/9535 |
| 2020/0194121 A1* | 6/2020 | Kupershmidt | G16H 50/20 |
| 2021/0241927 A1* | 8/2021 | Langdon | G16Y 40/20 |
| 2021/0297167 A1* | 9/2021 | Chen | G08B 21/18 |
| 2021/0312355 A1* | 10/2021 | Reber | G06Q 10/067 |

* cited by examiner

*Primary Examiner* — Jeanette J Parker
(74) *Attorney, Agent, or Firm* — Guntin & Gust, PLC; Robert Gingher

(57) ABSTRACT

Aspects of the subject disclosure may include, for example, a virtual assistant that includes a processing system including a processor; and a memory that stores executable instructions that, when executed by the processing system, facilitate performance of operations of creating a normalized profile for a user of the virtual assistant device; identifying an anomaly deviating from the normalized profile over a threshold time period during use of the virtual assistant device; and changing an interface of the virtual assistant device to accommodate the identified anomaly. Other embodiments are disclosed.

20 Claims, 8 Drawing Sheets

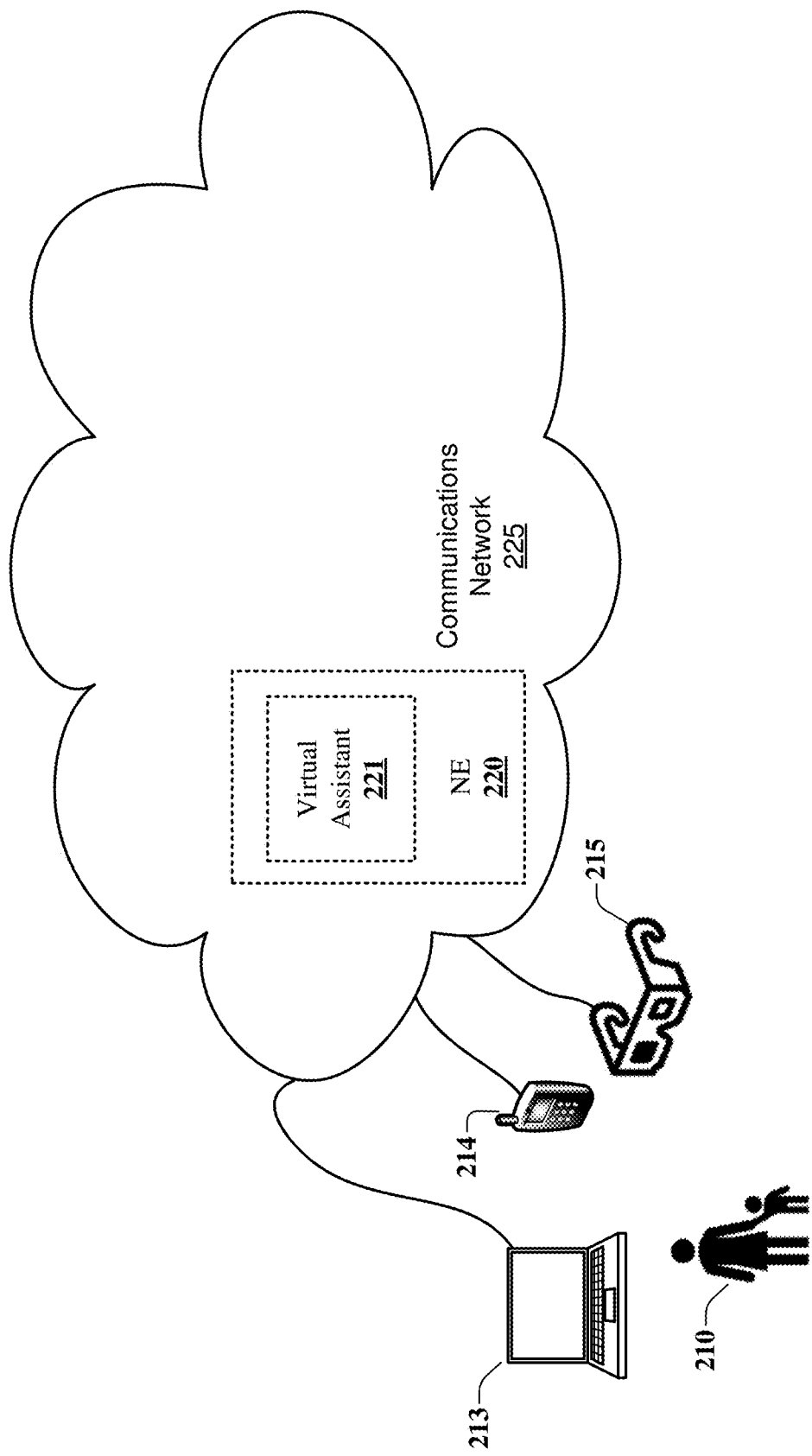

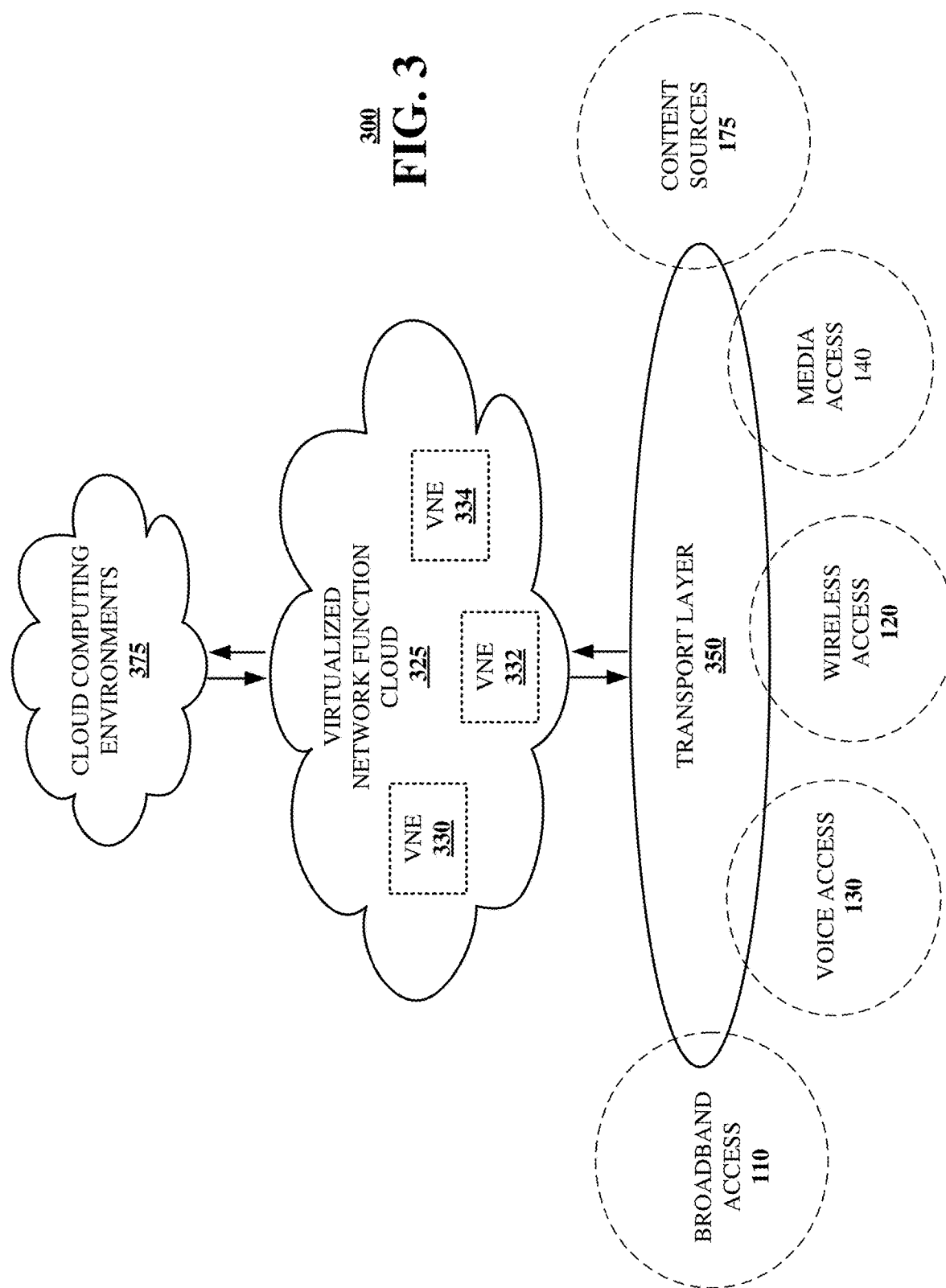

SYSTEM AND METHOD FOR AN ADAPTABLE, SMART VIRTUAL ASSISTANT THAT SUPPORTS LONG TERM CARE

FIELD OF THE DISCLOSURE

The subject disclosure relates to a system and method for an adaptable, smart virtual assistant that supports long term care.

BACKGROUND

A dialogue system, or conversational agent, is a computer system programmed to converse with a human. Dialogue systems engage users via one or more of text, speech, graphics, haptics, gestures, and other modes for communication on both the input and output devices. A dialogue system used to perform tasks or services for an individual based on commands or questions is known as a smart virtual assistant (VA). In 1952, Bell Labs created an automatic digit recognition machine dubbed "Audrey" that occupied a six-foot high relay rack, consumed substantial power, had streams of cables and exhibited the myriad maintenance problems associated with its complex vacuum-tube circuitry. See, e.g., U.S. Pat. No. 2,685,615. Nevertheless, Audrey could recognize the fundamental units of speech, called phonemes, and was limited to accurate recognition of digits zero through nine spoken by a particular speaker, and thus could functionally provide voice dialing. Today, many smart VAs can interpret human speech and respond via synthesized voices.

BRIEF DESCRIPTION OF THE DRAWINGS

Reference will now be made to the accompanying drawings, which are not necessarily drawn to scale, and wherein:

FIG. 2A is a block diagram illustrating an example, non-limiting embodiment of a system including a smart virtual assistant functioning within the communication network of FIG. 1 in accordance with various aspects described herein.

FIG. 3 is a block diagram illustrating an example, non-limiting embodiment of a virtualized communication network in accordance with various aspects described herein.

DETAILED DESCRIPTION

The subject disclosure describes, among other things, illustrative embodiments for a long-term virtual assistant. Other embodiments are described in the subject disclosure.

One or more aspects of the subject disclosure include a virtual assistant device that includes a processing system including a processor; and a memory that stores executable instructions that, when executed by the processing system, facilitate performance of operations of creating a normalized profile for a user of the virtual assistant device; identifying an anomaly deviating from the normalized profile over a threshold time period during use of the virtual assistant device; and changing an interface of the virtual assistant device to accommodate the identified anomaly.

One or more aspects of the subject disclosure include a non-transitory, machine-readable medium, comprising executable instructions that, when executed by a processing system including a processor, facilitate performance of operations including creating a behavior model for a user of a virtual assistant device; identifying an anomaly in a behavior of the user that deviates from the behavior model over a threshold time period during use of the virtual assistant device; and changing an interface of the virtual assistant device to accommodate the identified anomaly.

One or more aspects of the subject disclosure include a method of selecting, by a processing system including a processor, a behavior model for a user of a virtual assistant device; identifying, by the processing system, an anomaly in a behavior of the user that deviates from the behavior model over a threshold time period during use of the virtual assistant device; and adapting, by the processing system, an interface of the virtual assistant device responsive to the identified anomaly.

Figure 1:
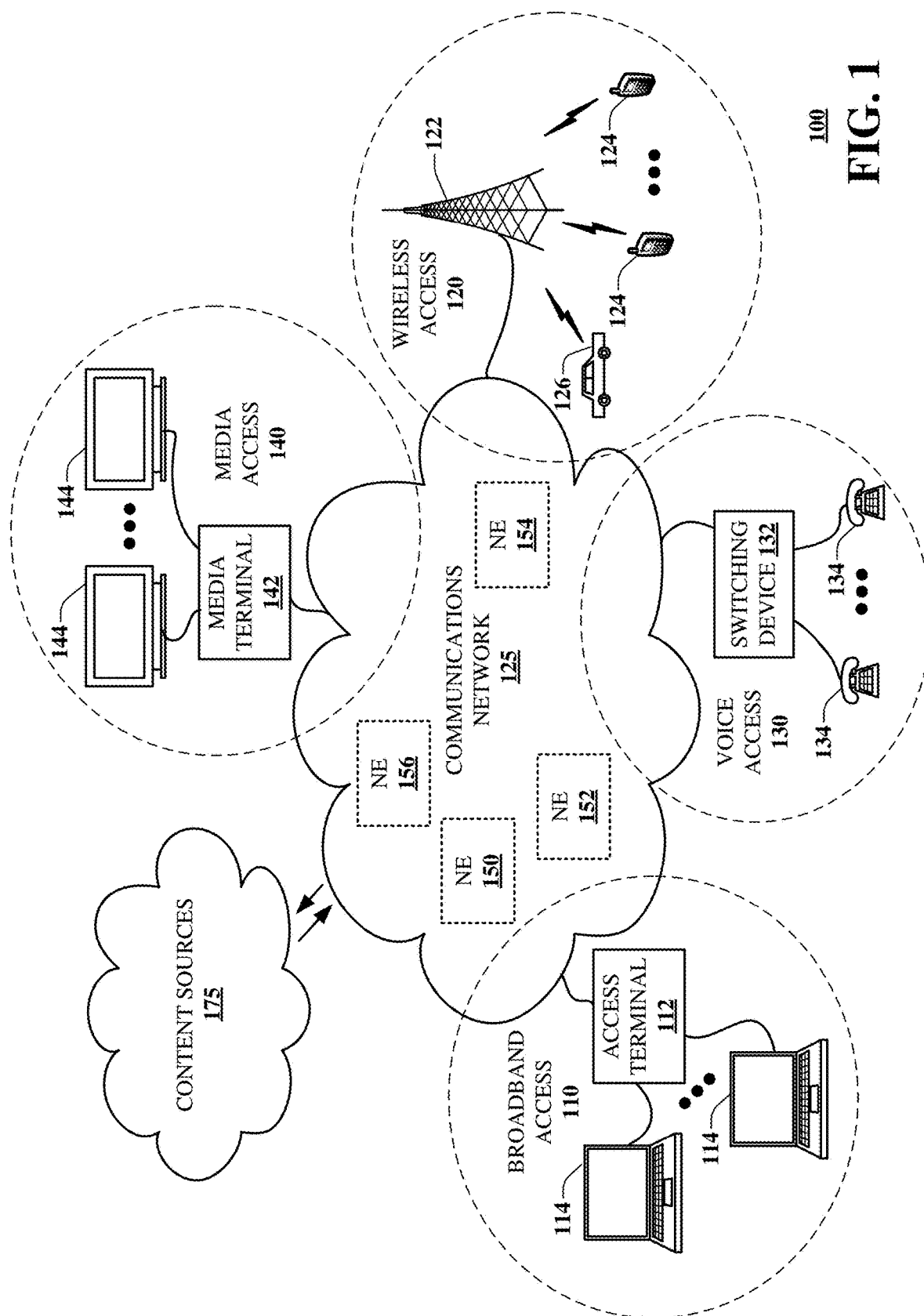
FIG. 1 is a block diagram illustrating an exemplary, non-limiting embodiment of a communications network in accordance with various aspects described herein.

Referring now to FIG. 1, a block diagram is shown illustrating an example, non-limiting embodiment of a system 100 in accordance with various aspects described herein. For example, system 100 can facilitate in whole or in part creating a behavior model for a user of a virtual assistant, identifying a behavioral anomaly of the user over a threshold time period using the virtual assistant, and adapting an interface of the virtual assistant responsive to the identified anomaly. In particular, a communications network 125 is presented for providing broadband access 110 to a plurality of data terminals 114 via access terminal 112, wireless access 120 to a plurality of mobile devices 124 and vehicle 126 via base station or access point 122, voice access 130 to a plurality of telephony devices 134, via switching device 132 and/or media access 140 to a plurality of audio/video display devices 144 via media terminal 142. In addition, communication network 125 is coupled to one or more content sources 175 of audio, video, graphics, text and/or other media. While broadband access 110, wireless access 120, voice access 130 and media access 140 are shown separately, one or more of these forms of access can be combined to provide multiple access services to a single client device (e.g., mobile devices 124 can receive media content via media terminal 142, data terminal 114 can be provided voice access via switching device 132, and so on).

The communications network 125 includes a plurality of network elements (NE) 150, 152, 154, 156, etc. for facilitating the broadband access 110, wireless access 120, voice access 130, media access 140 and/or the distribution of content from content sources 175. The communications network 125 can include a circuit switched or packet switched network, a voice over Internet protocol (VoIP) network, Internet protocol (IP) network, a cable network, a passive or active optical network, a 4G, 5G, or higher generation wireless access network, WIMAX network, UltraWideband network, personal area network or other wireless access network, a broadcast satellite network and/or other communications network.

In various embodiments, the access terminal 112 can include a digital subscriber line access multiplexer (DSLAM), cable modem termination system (CMTS), optical line terminal (OLT) and/or other access terminal. The data terminals 114 can include personal computers, laptop computers, netbook computers, tablets or other computing devices along with digital subscriber line (DSL) modems, data over coax service interface specification (DOCSIS) modems or other cable modems, a wireless modem such as a 4G, 5G, or higher generation modem, an optical modem and/or other access devices.

In various embodiments, the base station or access point 122 can include a 4G, 5G, or higher generation base station, an access point that operates via an 802.11 standard such as 802.11n, 802.11ac or other wireless access terminal. The mobile devices 124 can include mobile phones, e-readers, tablets, phablets, wireless modems, and/or other mobile computing devices.

In various embodiments, the switching device 132 can include a private branch exchange or central office switch, a media services gateway, VoIP gateway or other gateway device and/or other switching device. The telephony devices 134 can include traditional telephones (with or without a terminal adapter), VoIP telephones and/or other telephony devices.

In various embodiments, the media terminal 142 can include a cable head-end or other TV head-end, a satellite receiver, gateway or other media terminal 142. The display devices 144 can include televisions with or without a set top box, personal computers and/or other display devices.

In various embodiments, the content sources 175 include broadcast television and radio sources, video on demand platforms and streaming video and audio services platforms, one or more content data networks, data servers, web servers and other content servers, and/or other sources of media.

In various embodiments, the communications network 125 can include wired, optical and/or wireless links and the network elements 150, 152, 154, 156, etc. can include service switching points, signal transfer points, service control points, network gateways, media distribution hubs, servers, firewalls, routers, edge devices, switches and other network nodes for routing and controlling communications traffic over wired, optical and wireless links as part of the Internet and other public networks as well as one or more private networks, for managing subscriber access, for billing and network management and for supporting other network functions.

FIG. 2A is a block diagram illustrating an example, non-limiting embodiment of a system including a smart virtual assistant (VA) functioning within the communication network of FIG. 1 in accordance with various aspects described herein. As shown in FIG. 2A, system 200 comprises a variety of devices to provide a user 210 with a variety of different modes of communication with the VA 221. Such devices include a data terminal 213, a mobile device 214, or a virtual reality (VR) or augmented reality (AR) headset 215 that enable the user to converse with a VA 221 via text, speech, graphics, haptics, gestures, as well as provide other data on a condition of the user 210.

In an embodiment illustrated in FIG. 2A, smart virtual assistant 221 is embedded in a network element 220 within communications network 225, but other embodiments are contemplated, such as a stand-alone machine, like coding embedded in data terminal 213, mobile device 214 or headset 215, or in a distributed computing environment. As VA 221 becomes a more integral part of the daily interactions with user 210, VA 221 becomes more situationally aware and adaptable. For example, as user 210 ages, she may begin to process information more slowly, or develop cognitive issues, and may desire VA 221 to begin to present information in different visual ways, or slower audibly. VA 221 will be able to monitor for behavioral anomalies of user 210 as VA 221 they follow us through our life spans during which they need to adapt to best be our assistants, make our lives better and easier.

In an embodiment, VA 221 recognizes in a personal environment of user 210 to discover alternate ways for VA 221 to interact in a different (shorter, faster, longer, voice intonation, louder) way. VA 221 uses analytics to change the interface to user 210 that may not be directly on VA 221. In an embodiment, after detecting changes in behavior, VA 221 can propose alternate user experience configurations that interact with remotes, web pages, calendars, etc.

VA 221 monitors behaviors over a threshold time period (weeks, months or years) to discover long-horizon and potentially indirect conditions (e.g., detected depression, cognitive or physical degradations) that may require additional behavioral changes or external assistance (e.g., calling a friend or seeking medical advice). VA 221 may interface with different VAs (and non-VA devices) to orchestrate a change for the user 210 based on a use profile and detected behavioral detection, specifically solve for those anomalies or events by system interactions (e.g., VA 221 may specifically control a TV to be louder when user 210 is exercising, etc.). VA 221 may analyze an impact of different orchestrations for long-term behavioral challenges (e.g., first attempting louder content or increased connectivity to social connections). VA 221 may continue long-term monitoring but can be slightly automated by condition and response testing before escalation to family and care provider alerts.

In an embodiment, VA 221 uses short- and long-term aggregations of behaviors (e.g., speed for interaction, frequency of asking for repeats, etc.) to create a normalized profile for a person (and among cohorts of people, i.e., having similar characteristics) to build a behavioral model. The normalized profile may include metrics for expected user performance interacting with the virtual assistant, such as expected user response time or frequency of usage. These models may be coupled with traditional cognitive monitoring or subject matter expert monitoring, such as geriatric care, or age-related models versus injury, or identifying behavioral differences that may be detected and addressed independently. Predictive and reactive cognitive monitoring for VA 221 change proposals—combining both reactive analysis of behavioral changes (above), also accommodate predictive needs where one or more formal models have been created (from above cohorts or traditional cognitive degradation) where VA 221 creates changes in its interactions for both situations.

In an embodiment, VA 221 may propose or implement modifications for the user experience, including changes to graphical displays, voice controls, audio and visual properties of those interactions, and a "memory model" of how frequently VA 221 will proactively prompt the user for reminders or reaction times.

Figure 2B:
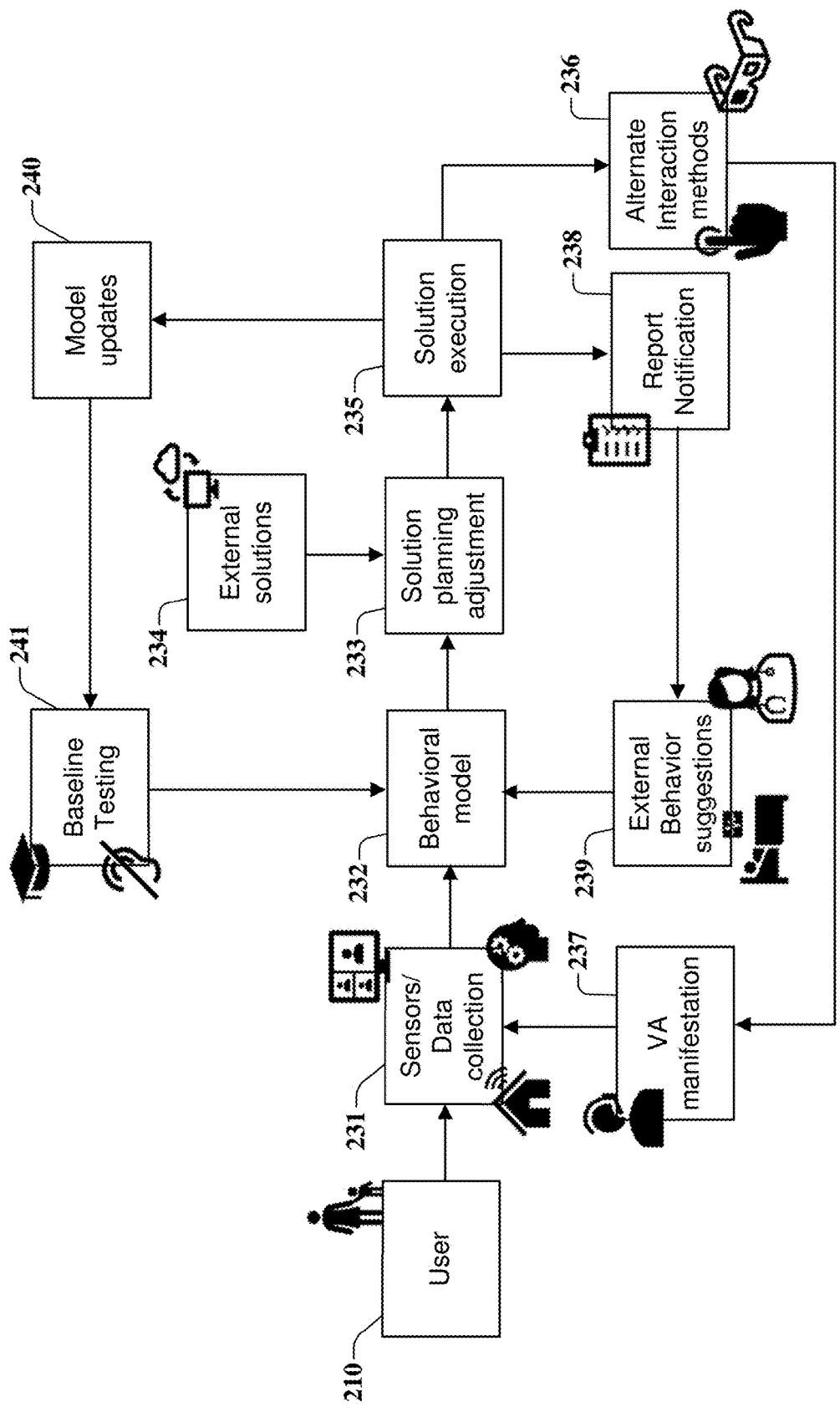
FIG. 2B is a system flowchart diagram depicting an illustrative embodiment of a method performed by a virtual assistant in accordance with various aspects described herein.

FIG. 2B is a system flowchart diagram depicting an illustrative embodiment of a method performed by a virtual assistant in accordance with various aspects described herein. As shown in FIG. 2B, in step 231, a VA that aids a user 210 attaches to a sensor environment of the user to gather data. In an embodiment, the VA may identify mobility or joint issues of the user. The VA may create a profile of the user's home and identify potential areas of greater risk of injury or falling.

Next, in step 232, the VA continuously monitors user interactions to establish a behavioral model. The VA may include optical data (e.g., an object is now in the way of walking path, discovers the user slipping, etc.) as reactionary observations. The VA may consider the user's interaction speed with the VA. The VA may create cognitive assessments for reading comprehension, interaction speed, familiarity with a topic or calendar appointments, medicine consumption, etc. Finally, the VA may recognize behavioral changes indicating that the user is deviating from a normal routine (not leaving the house, failing to call friends, etc.). The VA may discover challenges or trouble with user interactions on regular cadence (daily, hourly, event based, etc.). For a child, the VA may discover that they no longer need slow reading of a book or captions to understand the content (e.g., the child's reading comprehension and ability has improved). In another example, the VA may discover anomalous sleeping time in conjunction with poor cognitive or interaction performance, i.e., for a new parent or a user with negative stress or poor sleep habits.

Next in step 233, the VA itemizes proposed solutions for the behavioral anomalies recognized. In an embodiment, anomalies that were lower in priority (e.g., being overweight) are reweighted over time and include other behavioral observations (e.g., not exercising, bad diet, etc.).

Next in step 234, the VA optionally consults the Internet for solutions to the detected anomalies. In one embodiment, this consultation may only include information from the sensors (step 231) and activity that the user is currently executing. In another embodiment, the consultation may include a diverse list of anomalous behaviors determined by the behavioral model (step 232). In either of these embodiments, the response from the Internet may include potential solutions (step 233), additional baselines for testing (see step 241), or additional behavioral targets (see step 239) that are commonly associated with the sensor data or behavioral model anomalies.

Next in step 235, the VA executes solutions, such as modifying interactions with the user. The VA implements changes that are incorporated with direct interactions with the user.

Then in step 236, alternate interaction proposals are determined. Such alternate interaction proposals can be modifications of user experience, i.e., changes to the interactions with the user. The VA can present an interactive summary to the user for both proposing a life change (e.g., drink more milk) and the evidence supporting such life change.

Further in step 237, the VA might find other sensor points in home Internet-of-things (IoT) devices or other applications that may be useful to the VA in discovering limitations and standard behaviors of the user. Changes based on other IoT devices are pushed and evaluated over time to discover remediations for the anomalous component. The proposed changes are implemented by the VA. In another embodiment, additional capabilities that were not previously part of the VA may be added to accommodate newly discovered needs of the user 210. For example, the VA may propose one or more "safe words" that will immediately trigger calls to emergency service providers (medical, civil, familial) without explicit specification by the user. This discover and enablement of new features allows safety and care facilities to be enabled that the user may not be aware of but could benefit from if enabled automatically.

In addition, the solutions executed by the VA continue in step 238, where the VA can create regular cadence reports/plans and presents them to the user. The VA can optionally become more aggressive if the user continuously ignores warnings and interaction reports. Optionally, an insurer or provider may incentivize the user to fix or improve their environment.

In step 239, the VA may accept testing suggestions from professionals or family to assert and evaluate current cognitive capabilities (e.g., memory, familiarity, logic). The VA can generate reports for specific care providers for discovered anomalies/solutions and a check by other care providers associated with the user. In another embodiment, the VA may attempt to proactively enable behaviors that can help to reverse or stall the progression of the anomaly. For example, to stall progress of memory loss, the VA may prompt the user to talk about her or his family. In another example, the VA may attempt to connect the user to collaborative- or community-based gatherings of friends or family, either through digital means or by arranging an event or meeting on the user's behalf.

Further, the solutions executed by the VA continue in step 240, where the VA provides continuous updates and feedback with the user and constructs behavioral models and model updates.

In step 241, baseline models for a user profile and solutions can be used for discovery and prediction against other users in a cohort of users. These baselines may be managed and stored by the user's local VA 221 or distributed through communications networks 225 to other internet-based sources and external solutions providers 234.

Figure 2C:
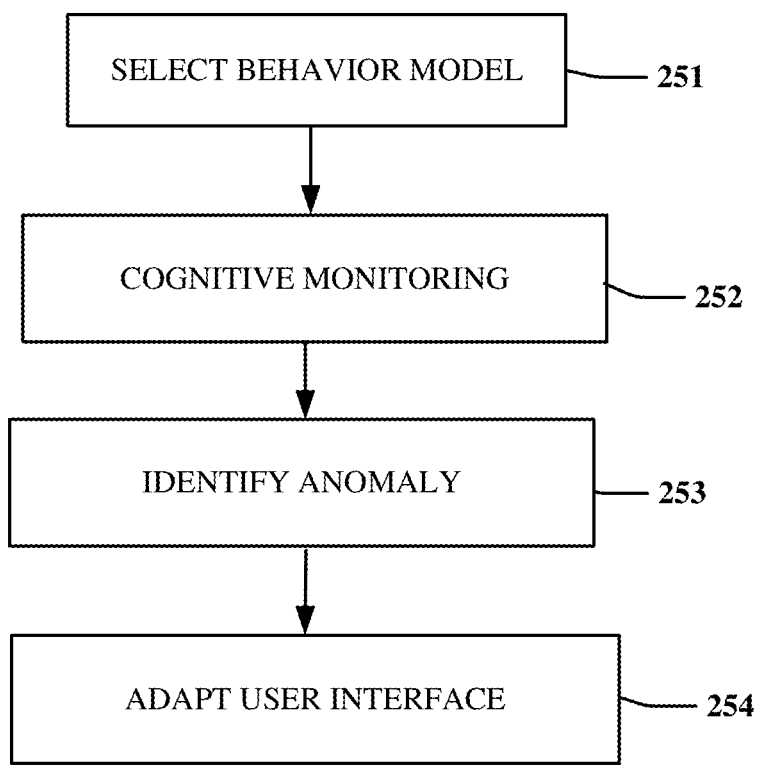
FIG. 2C is a flowchart diagram depicting an illustrative embodiment of a method performed by a system in accordance with various aspects described herein.

FIG. 2C is a flowchart diagram depicting an illustrative embodiment of a method 250 performed by a system in accordance with various aspects described herein. As shown in FIG. 2C, in step 251 the system selects a behavior model for a user of a virtual assistant from a number of behavioral models developed from users with similar characteristics.

In step 252, the system optionally performs cognitive monitoring of the user. Such cognitive monitoring may include assessments for reading comprehension, interaction speed, familiarity with a topic or calendar appointments, medicine consumption, frequency of requests, or a combination thereof.

In step 253, the system identifies an anomaly in a behavior of the user. The system may recognize a behavior of the user that deviates the behavior model over a threshold time period during use of the virtual assistant. Or the system may identify the anomaly from the cognitive monitoring or through pattern matching.

Finally, in step 254, the system adapts an interface of the virtual assistant responsive to the identified anomaly. In one embodiment, the adaptation may modify direct interactions between the VA 221 and the user 210, like response time, expert or novice help modes, volume, speed of interactions, etc. In another embodiment, the modality of interaction with the user 210 and the VA 221 may change from touch-typing (requiring tactile, fine-motor skills) to gesture- or speech-based controls (still cognitively demanding, but less reliant on hand-eye coordination). In yet another embodiment, the adaptation may modify interactions with other manifestations (step 232) and sensors (step 231) attached to the VA 221 throughout the user's home or communications network 225. For example, textual displays on a computer monitor or television may be instructed to render in a larger font, tactile interactions (e.g., touch screens, etc.) may draw buttons with a larger surface area or allow longer press/release timings to accommodate poorer muscle control by the aging user 210, or a VA 221 may preemptively turn on and off lights in a user's home as the user 210 navigates where previously explicit requests to the VA were required.

While for purposes of simplicity of explanation, the respective processes are shown and described as a series of blocks in FIGS. 2B and 2C, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Referring now to FIG. 3, a block diagram 300 is shown illustrating an example, non-limiting embodiment of a virtualized communication network in accordance with various aspects described herein. In particular a virtualized communication network is presented that can be used to implement some or all of the subsystems and functions of system 100, the subsystems and functions of system 200, and method 230 presented in FIGS. 1, 2A, 2B, 2C and 3. For example, virtualized communication network 300 can facilitate in whole or in part creating a behavior model for a user of a virtual assistant, identifying a behavioral anomaly of the user over a threshold time period using the virtual assistant, and adapting an interface of the virtual assistant responsive to the identified anomaly.

In particular, a cloud networking architecture is shown that leverages cloud technologies and supports rapid innovation and scalability via a transport layer 350, a virtualized network function cloud 325 and/or one or more cloud computing environments 375. In various embodiments, this cloud networking architecture is an open architecture that leverages application programming interfaces (APIs); reduces complexity from services and operations; supports more nimble business models; and rapidly and seamlessly scales to meet evolving customer requirements including traffic growth, diversity of traffic types, and diversity of performance and reliability expectations.

In contrast to traditional network elements—which are typically integrated to perform a single function, the virtualized communication network employs virtual network elements (VNEs) 330, 332, 334, etc. that perform some or all of the functions of network elements 150, 152, 154, 156, etc. For example, the network architecture can provide a substrate of networking capability, often called Network Function Virtualization Infrastructure (NFVI) or simply infrastructure that is capable of being directed with software and Software Defined Networking (SDN) protocols to perform a broad variety of network functions and services. This infrastructure can include several types of substrates. The most typical type of substrate being servers that support Network Function Virtualization (NFV), followed by packet forwarding capabilities based on generic computing resources, with specialized network technologies brought to bear when general-purpose processors or general-purpose integrated circuit devices offered by merchants (referred to herein as merchant silicon) are not appropriate. In this case, communication services can be implemented as cloud-centric workloads.

As an example, a traditional network element 150 (shown in FIG. 1), such as an edge router can be implemented via a VNE 330 composed of NFV software modules, merchant silicon, and associated controllers. The software can be written so that increasing workload consumes incremental resources from a common resource pool, and moreover so that it is elastic: so, the resources are only consumed when needed. In a similar fashion, other network elements such as other routers, switches, edge caches, and middle boxes are instantiated from the common resource pool. Such sharing of infrastructure across a broad set of uses makes planning and growing infrastructure easier to manage.

In an embodiment, the transport layer 350 includes fiber, cable, wired and/or wireless transport elements, network elements and interfaces to provide broadband access 110, wireless access 120, voice access 130, media access 140 and/or access to content sources 175 for distribution of content to any or all of the access technologies. In particular, in some cases a network element needs to be positioned at a specific place, and this allows for less sharing of common infrastructure. Other times, the network elements have specific physical layer adapters that cannot be abstracted or virtualized and might require special DSP code and analog front ends (AFEs) that do not lend themselves to implementation as VNEs 330, 332 or 334. These network elements can be included in transport layer 350.

The virtualized network function cloud 325 interfaces with the transport layer 350 to provide the VNEs 330, 332, 334, etc. to provide specific NFVs. In particular, the virtualized network function cloud 325 leverages cloud operations, applications, and architectures to support networking workloads. The virtualized network elements 330, 332 and 334 can employ network function software that provides either a one-for-one mapping of traditional network element function or alternately some combination of network functions designed for cloud computing. For example, VNEs 330, 332 and 334 can include route reflectors, domain name system (DNS) servers, and dynamic host configuration protocol (DHCP) servers, system architecture evolution (SAE) and/or mobility management entity (MME) gateways, broadband network gateways, IP edge routers for IP-VPN, Ethernet and other services, load balancers, distributers and other network elements. Because these elements do not typically need to forward large amounts of traffic, their workload can be distributed across a number of servers—each of which adds a portion of the capability, and which overall creates an elastic function with higher availability than its former monolithic version. These virtual network elements 330, 332, 334, etc. can be instantiated and managed using an orchestration approach similar to those used in cloud compute services.

The cloud computing environments 375 can interface with the virtualized network function cloud 325 via APIs that expose functional capabilities of the VNEs 330, 332, 334, etc. to provide the flexible and expanded capabilities to the virtualized network function cloud 325. In particular, network workloads may have applications distributed across the virtualized network function cloud 325 and cloud computing environment 375 and in the commercial cloud or might simply orchestrate workloads supported entirely in NFV infrastructure from these third-party locations.

Figure 4:
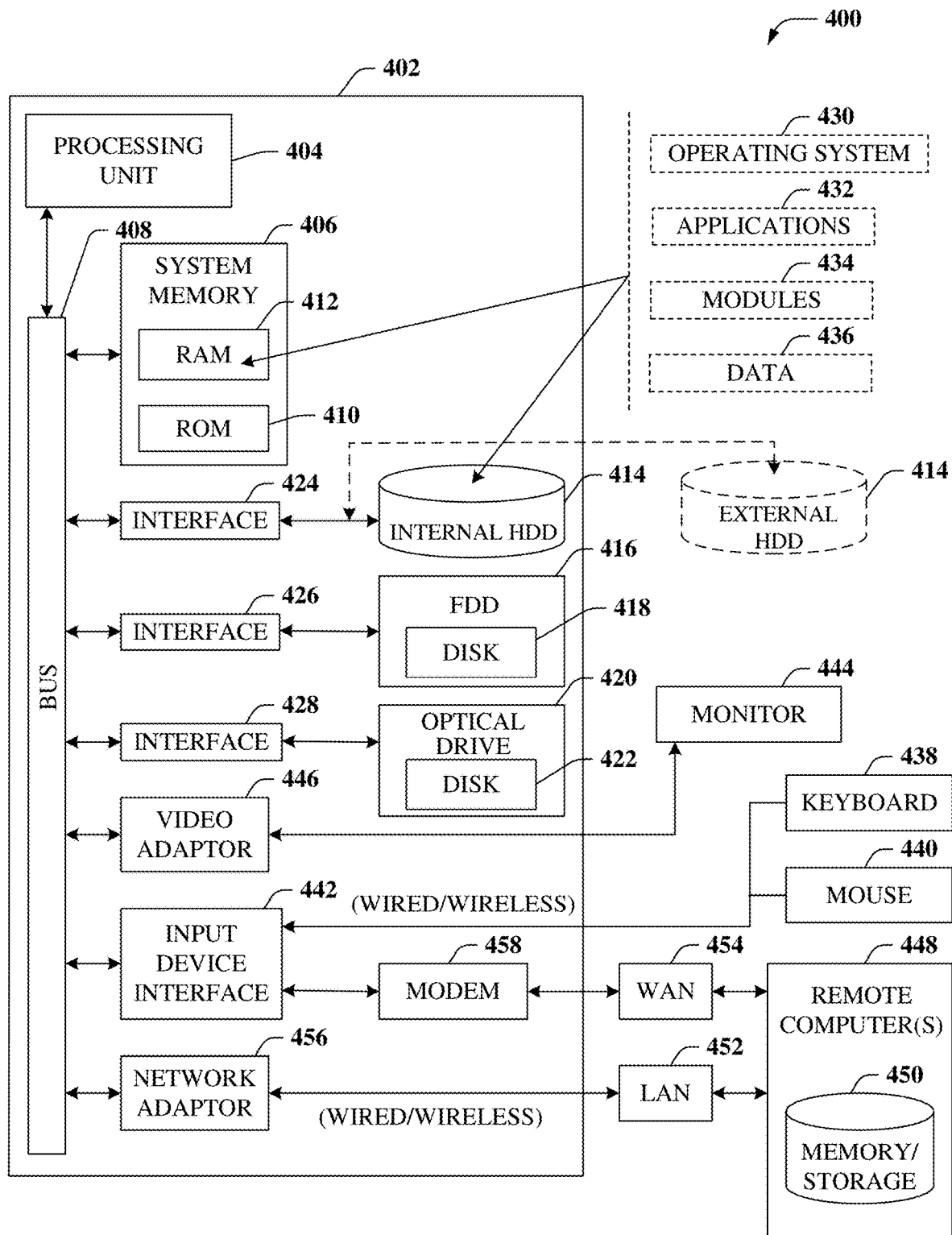
FIG. 4 is a block diagram of an example, non-limiting embodiment of a computing environment in accordance with various aspects described herein.

Turning now to FIG. 4, there is illustrated a block diagram of a computing environment in accordance with various aspects described herein. In order to provide additional context for various embodiments of the embodiments described herein, FIG. 4 and the following discussion are intended to provide a brief, general description of a suitable computing environment 400 in which the various embodiments of the subject disclosure can be implemented. In particular, computing environment 400 can be used in the implementation of network elements 150, 152, 154, 156, access terminal 112, base station or access point 122, switching device 132, media terminal 142, and/or VNEs 330, 332, 334, etc. Each of these devices can be implemented via computer-executable instructions that can run on one or more computers, and/or in combination with other program modules and/or as a combination of hardware and software. For example, computing environment 400 can facilitate in whole or in part creating a behavior model for a user of a virtual assistant, identifying a behavioral anomaly of the user over a threshold time period using the virtual assistant, and adapting an interface of the virtual assistant responsive to the identified anomaly.

Generally, program modules comprise routines, programs, components, data structures, etc., that perform particular tasks or implement particular abstract data types. Moreover, those skilled in the art will appreciate that the methods can be practiced with other computer system configurations, comprising single-processor or multiprocessor computer systems, minicomputers, mainframe computers, as well as personal computers, hand-held computing devices, microprocessor-based or programmable consumer electronics, and the like, each of which can be operatively coupled to one or more associated devices.

As used herein, a processing circuit includes one or more processors as well as other application specific circuits such as an application specific integrated circuit, digital logic circuit, state machine, programmable gate array or other circuit that processes input signals or data and that produces output signals or data in response thereto. It should be noted that while any functions and features described herein in association with the operation of a processor could likewise be performed by a processing circuit.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically comprise a variety of media, which can comprise computer-readable storage media and/or communications media, which two terms are used herein differently from one another as follows. Computer-readable storage media can be any available storage media that can be accessed by the computer and comprises both volatile and nonvolatile media, removable and non-removable media. By way of example, and not limitation, computer-readable storage media can be implemented in connection with any method or technology for storage of information such as computer-readable instructions, program modules, structured data or unstructured data.

Computer-readable storage media can comprise, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage or other magnetic storage devices or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and comprises any information delivery or transport media. The term "modulated data signal" or signals refers to a signal that has one or more of its characteristics set or changed in such a manner as to encode information in one or more signals. By way of example, and not limitation, communication media comprise wired media, such as a wired network or direct-wired connection, and wireless media such as acoustic, RF, infrared and other wireless media.

With reference again to FIG. 4, the example environment can comprise a computer 402, the computer 402 comprising a processing unit 404, a system memory 406 and a system bus 408. The system bus 408 couples system components including, but not limited to, the system memory 406 to the processing unit 404. The processing unit 404 can be any of various commercially available processors. Dual microprocessors and other multiprocessor architectures can also be employed as the processing unit 404.

The system bus 408 can be any of several types of bus structure that can further interconnect to a memory bus (with or without a memory controller), a peripheral bus, and a local bus using any of a variety of commercially available bus architectures. The system memory 406 comprises ROM 410 and RAM 412. A basic input/output system (BIOS) can be stored in a non-volatile memory such as ROM, erasable programmable read only memory (EPROM), EEPROM, which BIOS contains the basic routines that help to transfer information between elements within the computer 402, such as during startup. The RAM 412 can also comprise a high-speed RAM such as static RAM for caching data.

The computer 402 further comprises an internal hard disk drive (HDD) 414 (e.g., EIDE, SATA), which internal HDD 414 can also be configured for external use in a suitable chassis (not shown), a magnetic floppy disk drive (FDD) 416, (e.g., to read from or write to a removable diskette 418) and an optical disk drive 420, (e.g., reading a CD-ROM disk 422 or, to read from or write to other high-capacity optical media such as the DVD). The HDD 414, magnetic FDD 416 and optical disk drive 420 can be connected to the system bus 408 by a hard disk drive interface 424, a magnetic disk drive interface 426 and an optical drive interface 428, respectively. The hard disk drive interface 424 for external drive implementations comprises at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 402, the drives and storage media accommodate the storage of any data in a suitable digital format. Although the description of computer-readable storage media above refers to a hard disk drive (HDD), a removable magnetic diskette, and a removable optical media such as a CD or DVD, it should be appreciated by those skilled in the art that other types of storage media which are readable by a computer, such as zip drives, magnetic cassettes, flash memory cards, cartridges, and the like, can also be used in the example operating environment, and further, that any such storage media can contain computer-executable instructions for performing the methods described herein.

A number of program modules can be stored in the drives and RAM 412, comprising an operating system 430, one or more application programs 432, other program modules 434 and program data 436. All or portions of the operating system, applications, modules, and/or data can also be cached in the RAM 412. The systems and methods described herein can be implemented utilizing various commercially available operating systems or combinations of operating systems.

A user can enter commands and information into the computer 402 through one or more wired/wireless input devices, e.g., a keyboard 438 and a pointing device, such as a mouse 440. Other input devices (not shown) can comprise a microphone, an infrared (IR) remote control, a joystick, a game pad, a stylus pen, touch screen or the like. These and other input devices are often connected to the processing unit 404 through an input device interface 442 that can be coupled to the system bus 408, but can be connected by other interfaces, such as a parallel port, an IEEE 1394 serial port, a game port, a universal serial bus (USB) port, an IR interface, etc.

A monitor 444 or other type of display device can be also connected to the system bus 408 via an interface, such as a video adapter 446. It will also be appreciated that in alternative embodiments, a monitor 444 can also be any display device (e.g., another computer having a display, a smart phone, a tablet computer, etc.) for receiving display information associated with computer 402 via any communication means, including via the Internet and cloud-based networks. In addition to the monitor 444, a computer typically comprises other peripheral output devices (not shown), such as speakers, printers, etc.

The computer 402 can operate in a networked environment using logical connections via wired and/or wireless communications to one or more remote computers, such as a remote computer(s) 448. The remote computer(s) 448 can be a workstation, a server computer, a router, a personal computer, portable computer, microprocessor-based entertainment appliance, a peer device or other common network node, and typically comprises many or all of the elements described relative to the computer 402, although, for purposes of brevity, only a remote memory/storage device 450 is illustrated. The logical connections depicted comprise wired/wireless connectivity to a local area network (LAN) 452 and/or larger networks, e.g., a wide area network (WAN) 454. Such LAN and WAN networking environments are commonplace in offices and companies, and facilitate enterprise-wide computer networks, such as intranets, all of which can connect to a global communications network, e.g., the Internet.

When used in a LAN networking environment, the computer 402 can be connected to the LAN 452 through a wired and/or wireless communication network interface or adapter 456. The adapter 456 can facilitate wired or wireless communication to the LAN 452, which can also comprise a wireless AP disposed thereon for communicating with the adapter 456.

When used in a WAN networking environment, the computer 402 can comprise a modem 458 or can be connected to a communications server on the WAN 454 or has other means for establishing communications over the WAN 454, such as by way of the Internet. The modem 458, which can be internal or external and a wired or wireless device, can be connected to the system bus 408 via the input device interface 442. In a networked environment, program modules depicted relative to the computer 402 or portions thereof, can be stored in the remote memory/storage device 450. It will be appreciated that the network connections shown are example and other means of establishing a communications link between the computers can be used.

The computer 402 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This can comprise Wireless Fidelity (Wi-Fi) and BLUETOOTH® wireless technologies. Thus, the communication can be a predefined structure as with a conventional network or simply an ad hoc communication between at least two devices.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, n, ac, ag, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands for example or with products that contain both bands (dual band), so the networks can provide real-world performance similar to the basic 10BaseT wired Ethernet networks used in many offices.

Figure 5:
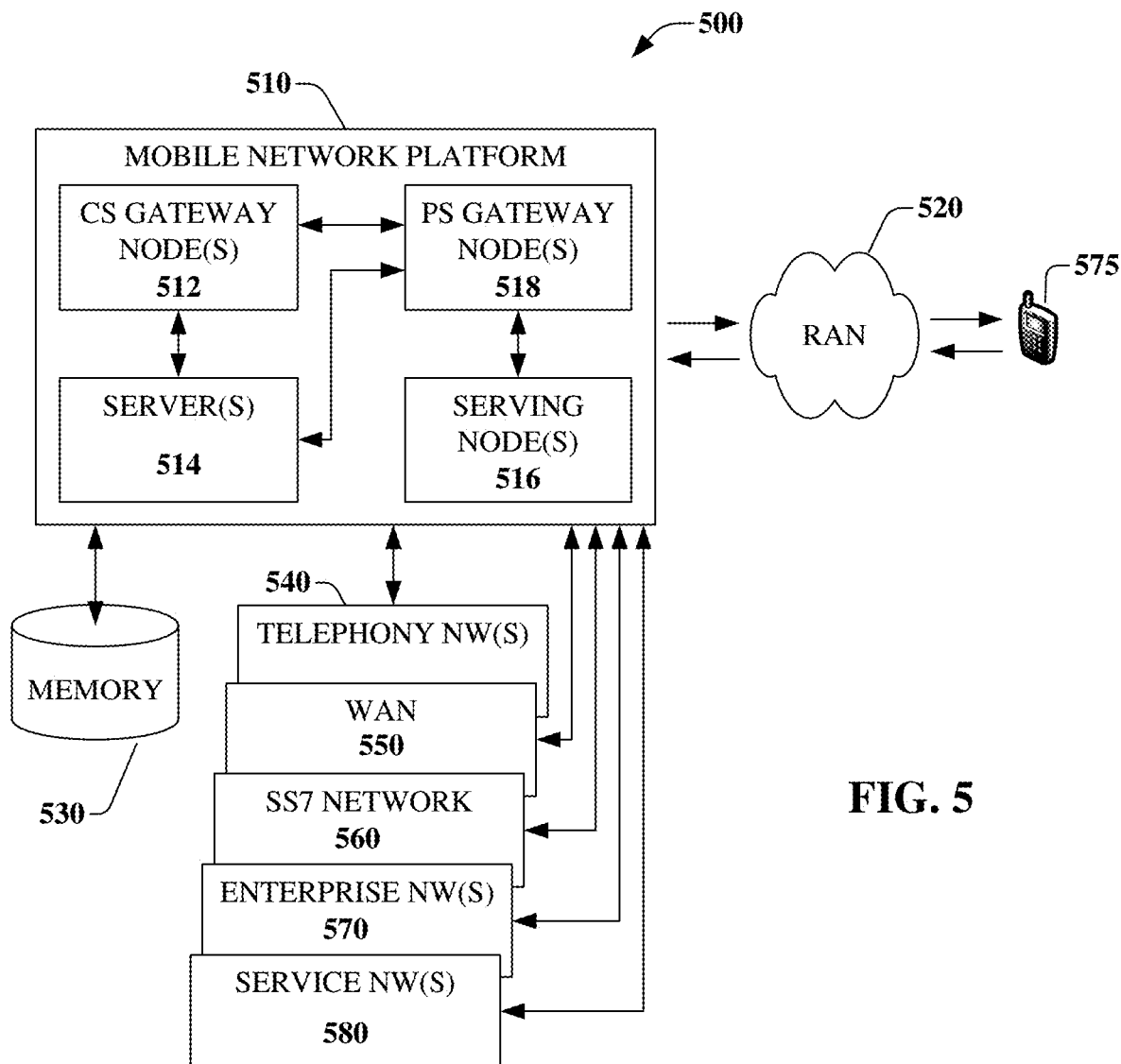
FIG. 5 is a block diagram of an example, non-limiting embodiment of a mobile network platform in accordance with various aspects described herein.

Turning now to FIG. 5, an embodiment 500 of a mobile network platform 510 is shown that is an example of network elements 150, 152, 154, 156, and/or VNEs 330, 332, 334, etc. For example, platform 510 can facilitate in whole or in part creating a behavior model for a user of a virtual assistant, identifying a behavioral anomaly of the user over a threshold time period using the virtual assistant, and adapting an interface of the virtual assistant responsive to the identified anomaly. In one or more embodiments, the mobile network platform 510 can generate and receive signals transmitted and received by base stations or access points such as base station or access point 122. Generally, mobile network platform 510 can comprise components, e.g., nodes, gateways, interfaces, servers, or disparate platforms, that facilitate both packet-switched (PS) (e.g., internet protocol (IP), frame relay, asynchronous transfer mode (ATM)) and circuit-switched (CS) traffic (e.g., voice and data), as well as control generation for networked wireless telecommunication. As a non-limiting example, mobile network platform 510 can be included in telecommunications carrier networks and can be considered carrier-side components as discussed elsewhere herein. Mobile network platform 510 comprises CS gateway node(s) 512 which can interface CS traffic received from legacy networks like telephony network(s) 540 (e.g., public switched telephone network (PSTN), or public land mobile network (PLMN)) or a signaling system #7 (SS7) network 560. CS gateway node(s) 512 can authorize and authenticate traffic (e.g., voice) arising from such networks. Additionally, CS gateway node(s) 512 can access mobility, or roaming, data generated through SS7 network 560; for instance, mobility data stored in a visited location register (VLR), which can reside in memory 530. Moreover, CS gateway node(s) 512 interfaces CS-based traffic and signaling and PS gateway node(s) 518. As an example, in a 3GPP UMTS network, CS gateway node(s) 512 can be realized at least in part in gateway GPRS support node(s) (GGSN). It should be appreciated that functionality and specific operation of CS gateway node(s) 512, PS gateway node(s) 518, and serving node(s) 516, is provided and dictated by radio technology (ies) utilized by mobile network platform 510 for telecommunication over a radio access network 520 with other devices, such as a radiotelephone 575.

In addition to receiving and processing CS-switched traffic and signaling, PS gateway node(s) 518 can authorize and authenticate PS-based data sessions with served mobile devices. Data sessions can comprise traffic, or content(s), exchanged with networks external to the mobile network platform 510, like wide area network(s) (WANs) 550, enterprise network(s) 570, and service network(s) 580, which can be embodied in local area network(s) (LANs), can also be interfaced with mobile network platform 510 through PS gateway node(s) 518. It is to be noted that WANs 550 and enterprise network(s) 570 can embody, at least in part, a service network(s) like IP multimedia subsystem (IMS). Based on radio technology layer(s) available in technology resource(s) or radio access network 520, PS gateway node(s) 518 can generate packet data protocol contexts when a data session is established; other data structures that facilitate routing of packetized data also can be generated. To that end, in an aspect, PS gateway node(s) 518 can comprise a tunnel interface (e.g., tunnel termination gateway (TTG) in 3GPP UMTS network(s) (not shown)) which can facilitate packetized communication with disparate wireless network(s), such as Wi-Fi networks.

In embodiment 500, mobile network platform 510 also comprises serving node(s) 516 that, based upon available radio technology layer(s) within technology resource(s) in the radio access network 520, convey the various packetized flows of data streams received through PS gateway node(s) 518. It is to be noted that for technology resource(s) that rely primarily on CS communication, server node(s) can deliver traffic without reliance on PS gateway node(s) 518; for example, server node(s) can embody at least in part a mobile switching center. As an example, in a 3GPP UMTS network, serving node(s) 516 can be embodied in serving GPRS support node(s) (SGSN).

For radio technologies that exploit packetized communication, server(s) 514 in mobile network platform 510 can execute numerous applications that can generate multiple disparate packetized data streams or flows, and manage (e.g., schedule, queue, format . . . ) such flows. Such application(s) can comprise add-on features to standard services (for example, provisioning, billing, customer support . . . ) provided by mobile network platform 510. Data streams (e.g., content(s) that are part of a voice call or data session) can be conveyed to PS gateway node(s) 518 for authorization/authentication and initiation of a data session, and to serving node(s) 516 for communication thereafter. In addition to application server, server(s) 514 can comprise utility server(s), a utility server can comprise a provisioning server, an operations and maintenance server, a security server that can implement at least in part a certificate authority and firewalls as well as other security mechanisms, and the like. In an aspect, security server(s) secure communication served through mobile network platform 510 to ensure network's operation and data integrity in addition to authorization and authentication procedures that CS gateway node(s) 512 and PS gateway node(s) 518 can enact. Moreover, provisioning server(s) can provision services from external network(s) like networks operated by a disparate service provider; for instance, WAN 550 or Global Positioning System (GPS) network(s) (not shown). Provisioning server(s) can also provision coverage through networks associated to mobile network platform 510 (e.g., deployed and operated by the same service provider), such as the distributed antennas networks shown in FIG. 1(*s*) that enhance wireless service coverage by providing more network coverage.

It is to be noted that server(s) 514 can comprise one or more processors configured to confer at least in part the functionality of mobile network platform 510. To that end, the one or more processors can execute code instructions stored in memory 530, for example. It should be appreciated that server(s) 514 can comprise a content manager, which operates in substantially the same manner as described hereinbefore.

In example embodiment 500, memory 530 can store information related to operation of mobile network platform 510. Other operational information can comprise provisioning information of mobile devices served through mobile network platform 510, subscriber databases; application intelligence, pricing schemes, e.g., promotional rates, flat-rate programs, couponing campaigns; technical specification(s) consistent with telecommunication protocols for operation of disparate radio, or wireless, technology layers; and so forth. Memory 530 can also store information from at least one of telephony network(s) 540, WAN 550, SS7 network 560, or enterprise network(s) 570. In an aspect, memory 530 can be, for example, accessed as part of a data store component or as a remotely connected memory store.

In order to provide a context for the various aspects of the disclosed subject matter, FIG. 5, and the following discussion, are intended to provide a brief, general description of a suitable environment in which the various aspects of the disclosed subject matter can be implemented. While the subject matter has been described above in the general context of computer-executable instructions of a computer program that runs on a computer and/or computers, those skilled in the art will recognize that the disclosed subject matter also can be implemented in combination with other program modules. Generally, program modules comprise routines, programs, components, data structures, etc. that perform particular tasks and/or implement particular abstract data types.

Figure 6:
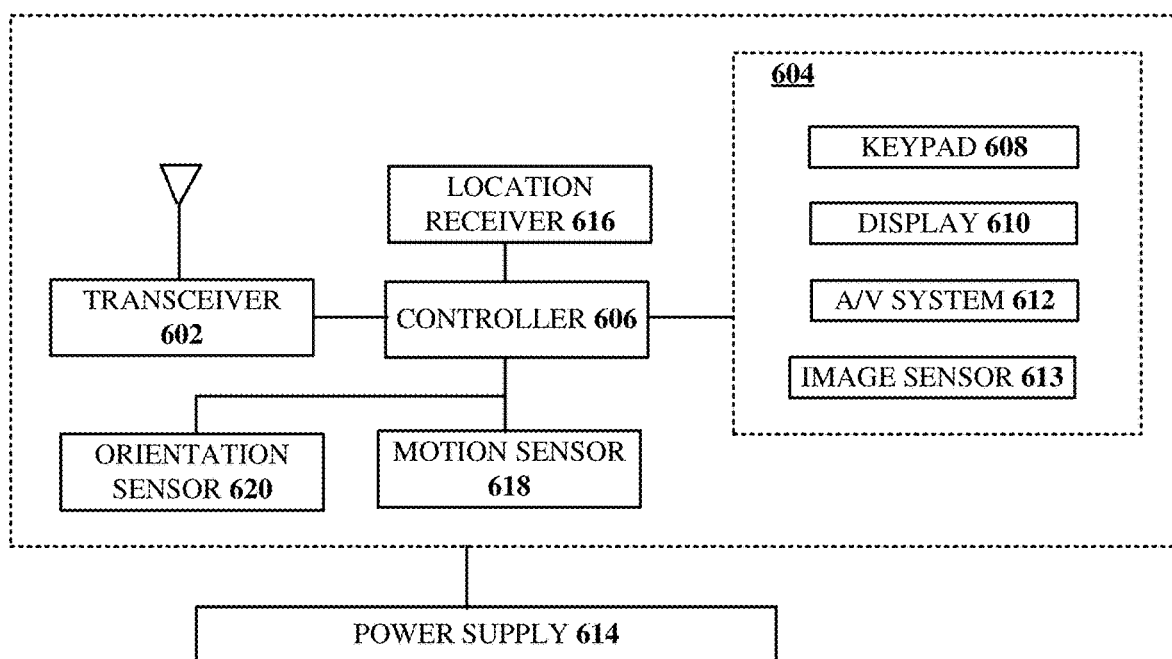
FIG. 6 is a block diagram of an example, non-limiting embodiment of a communication device in accordance with various aspects described herein.

Turning now to FIG. 6, an illustrative embodiment of a communication device 600 is shown. The communication device 600 can serve as an illustrative embodiment of devices such as data terminals 114, mobile devices 124, vehicle 126, display devices 144 or other client devices for communication via either communications network 125. For example, computing device 600 can facilitate in whole or in part creating a behavior model for a user of a virtual assistant, identifying a behavioral anomaly of the user over a threshold time period using the virtual assistant, and adapting an interface of the virtual assistant responsive to the identified anomaly.

The communication device 600 can comprise a wireline and/or wireless transceiver 602 (herein transceiver 602), a user interface (UI) 604, a power supply 614, a location receiver 616, a motion sensor 618, an orientation sensor 620, and a controller 606 for managing operations thereof. The transceiver 602 can support short-range or long-range wireless access technologies such as Bluetooth®, ZigBee®, Wi-Fi, DECT, or cellular communication technologies, just to mention a few (Bluetooth® and ZigBee® are trademarks registered by the Bluetooth® Special Interest Group and the ZigBee® Alliance, respectively). Cellular technologies can include, for example, CDMA-1X, UMTS/HSDPA, GSM/GPRS, TDMA/EDGE, EV/DO, WiMAX, SDR, LTE, as well as other next generation wireless communication technologies as they arise. The transceiver 602 can also be adapted to support circuit-switched wireline access technologies (such as PSTN), packet-switched wireline access technologies (such as TCP/IP, VoIP, etc.), and combinations thereof.

The UI 604 can include a depressible or touch-sensitive keypad 608 with a navigation mechanism such as a roller ball, a joystick, a mouse, or a navigation disk for manipulating operations of the communication device 600. The keypad 608 can be an integral part of a housing assembly of the communication device 600 or an independent device operably coupled thereto by a tethered wireline interface (such as a USB cable) or a wireless interface supporting for example Bluetooth®. The keypad 608 can represent a numeric keypad commonly used by phones, and/or a QWERTY keypad with alphanumeric keys. The UI 604 can further include a display 610 such as monochrome or color LCD (Liquid Crystal Display), OLED (Organic Light Emitting Diode) or other suitable display technology for conveying images to an end user of the communication device 600. In an embodiment where the display 610 is touch-sensitive, a portion or all of the keypad 608 can be presented by way of the display 610 with navigation features.

The display 610 can use touch screen technology to also serve as a user interface for detecting user input. As a touch screen display, the communication device 600 can be adapted to present a user interface having graphical user interface (GUI) elements that can be selected by a user with a touch of a finger. The display 610 can be equipped with capacitive, resistive or other forms of sensing technology to detect how much surface area of a user's finger has been placed on a portion of the touch screen display. This sensing information can be used to control the manipulation of the GUI elements or other functions of the user interface. The display 610 can be an integral part of the housing assembly of the communication device 600 or an independent device communicatively coupled thereto by a tethered wireline interface (such as a cable) or a wireless interface.

The UI 604 can also include an audio system 612 that utilizes audio technology for conveying low volume audio (such as audio heard in proximity of a human ear) and high-volume audio (such as speakerphone for hands free operation). The audio system 612 can further include a microphone for receiving audible signals of an end user. The audio system 612 can also be used for voice recognition applications. The UI 604 can further include an image sensor 613 such as a charged coupled device (CCD) camera for capturing still or moving images.

The power supply 614 can utilize common power management technologies such as replaceable and rechargeable batteries, supply regulation technologies, and/or charging system technologies for supplying energy to the components of the communication device 600 to facilitate long-range or short-range portable communications. Alternatively, or in combination, the charging system can utilize external power sources such as DC power supplied over a physical interface such as a USB port or other suitable tethering technologies.

The location receiver 616 can utilize location technology such as a global positioning system (GPS) receiver capable of assisted GPS for identifying a location of the communication device 600 based on signals generated by a constellation of GPS satellites, which can be used for facilitating location services such as navigation. The motion sensor 618 can utilize motion sensing technology such as an accelerometer, a gyroscope, or other suitable motion sensing technology to detect motion of the communication device 600 in three-dimensional space. The orientation sensor 620 can utilize orientation sensing technology such as a magnetometer to detect the orientation of the communication device 600 (north, south, west, and east, as well as combined orientations in degrees, minutes, or other suitable orientation metrics).

The communication device 600 can use the transceiver 602 to also determine a proximity to a cellular, Wi-Fi, Bluetooth®, or other wireless access points by sensing techniques such as utilizing a received signal strength indicator (RSSI) and/or signal time of arrival (TOA) or time of flight (TOF) measurements. The controller 606 can utilize computing technologies such as a microprocessor, a digital signal processor (DSP), programmable gate arrays, application specific integrated circuits, and/or a video processor with associated storage memory such as Flash, ROM, RAM, SRAM, DRAM or other storage technologies for executing computer instructions, controlling, and processing data supplied by the aforementioned components of the communication device 600.

Other components not shown in FIG. 6 can be used in one or more embodiments of the subject disclosure. For instance, the communication device 600 can include a slot for adding or removing an identity module such as a Subscriber Identity Module (SIM) card or Universal Integrated Circuit Card (UICC). SIM or UICC cards can be used for identifying subscriber services, executing programs, storing subscriber data, and so on.

The terms "first," "second," "third," and so forth, as used in the claims, unless otherwise clear by context, is for clarity only and does not otherwise indicate or imply any order in time. For instance, "a first determination," "a second determination," and "a third determination," does not indicate or imply that the first determination is to be made before the second determination, or vice versa, etc.

In the subject specification, terms such as "store," "storage," "data store," data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can comprise both volatile and nonvolatile memory, by way of illustration, and not limitation, volatile memory, non-volatile memory, disk storage, and memory storage. Further, nonvolatile memory can be included in read only memory (ROM), programmable ROM (PROM), electrically programmable ROM (EPROM), electrically erasable ROM (EEPROM), or flash memory. Volatile memory can comprise random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Moreover, it will be noted that the disclosed subject matter can be practiced with other computer system configurations, comprising single-processor or multiprocessor computer systems, mini-computing devices, mainframe computers, as well as personal computers, hand-held computing devices (e.g., PDA, phone, smartphone, watch, tablet computers, netbook computers, etc.), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

In one or more embodiments, information regarding use of services can be generated including services being accessed, media consumption history, user preferences, and so forth. This information can be obtained by various methods including user input, detecting types of communications (e.g., video content vs. audio content), analysis of content streams, sampling, and so forth. The generating, obtaining and/or monitoring of this information can be responsive to an authorization provided by the user. In one or more embodiments, an analysis of data can be subject to authorization from user(s) associated with the data, such as an opt-in, an opt-out, acknowledgement requirements, notifications, selective authorization based on types of data, and so forth.

Some of the embodiments described herein can also employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out various embodiments thereof. Moreover, the classifier can be employed to determine a ranking or priority of each cell site of the acquired network. A classifier is a function that maps an input attribute vector, $x=(x_1, x_2, x_3, x_4 \ldots x_n)$, to a confidence that the input belongs to a class, that is, $f(x)$=confidence(class). Such classification can employ a probabilistic and/or statistical-based analysis (e.g., factoring into the analysis utilities and costs) to determine or infer an action that a user desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches comprise, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing UE behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to predetermined criteria which of the acquired cell sites will benefit a maximum number of subscribers and/or which of the acquired cell sites will add minimum value to the existing communication network coverage, etc.

As used in some contexts in this application, in some embodiments, the terms "component," "system" and the like are intended to refer to, or comprise, a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, computer-executable instructions, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software or firmware that confers at least in part the functionality of the electronic components. While various components have been illustrated as separate components, it will be appreciated that multiple components can be implemented as a single component, or a single component can be implemented as multiple components, without departing from example embodiments.

Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer program accessible from any computer-readable device or computer-readable storage/communications media. For example, computer readable storage media can include, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, terms such as "user equipment," "mobile station," "mobile," subscriber station," "access terminal," "terminal," "handset," "mobile device" (and/or terms representing similar terminology) can refer to a wireless device utilized by a subscriber or user of a wireless communication service to receive or convey data, control, voice, video, sound, gaming or substantially any data-stream or signaling-stream. The foregoing terms are utilized interchangeably herein and with reference to the related drawings.

Furthermore, the terms "user," "subscriber," "customer," "consumer" and the like are employed interchangeably throughout, unless context warrants particular distinctions among the terms. It should be appreciated that such terms can refer to human entities or automated components supported through artificial intelligence (e.g., a capacity to make inference based, at least, on complex mathematical formalisms), which can provide simulated vision, sound recognition and so forth.

As employed herein, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of user equipment. A processor can also be implemented as a combination of computing processing units.

As used herein, terms such as "data storage," data storage," "database," and substantially any other information storage component relevant to operation and functionality of a component, refer to "memory components," or entities embodied in a "memory" or components comprising the memory. It will be appreciated that the memory components or computer-readable storage media, described herein can be either volatile memory or nonvolatile memory or can include both volatile and nonvolatile memory.

What has been described above includes mere examples of various embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

As may also be used herein, the term(s) "operably coupled to", "coupled to", and/or "coupling" includes direct coupling between items and/or indirect coupling between items via one or more intervening items. Such items and intervening items include, but are not limited to, junctions, communication paths, components, circuit elements, circuits, functional blocks, and/or devices. As an example of indirect coupling, a signal conveyed from a first item to a second item may be modified by one or more intervening items by modifying the form, nature or format of information in a signal, while one or more elements of the information in the signal are nevertheless conveyed in a manner than can be recognized by the second item. In a further example of indirect coupling, an action in a first item can cause a reaction on the second item, as a result of actions and/or reactions in one or more intervening items.

Although specific embodiments have been illustrated and described herein, it should be appreciated that any arrangement which achieves the same or similar purpose may be substituted for the embodiments described or shown by the subject disclosure. The subject disclosure is intended to cover any and all adaptations or variations of various embodiments. Combinations of the above embodiments, and other embodiments not specifically described herein, can be used in the subject disclosure. For instance, one or more features from one or more embodiments can be combined with one or more features of one or more other embodiments. In one or more embodiments, features that are positively recited can also be negatively recited and excluded from the embodiment with or without replacement by another structural and/or functional feature. The steps or functions described with respect to the embodiments of the subject disclosure can be performed in any order. The steps or functions described with respect to the embodiments of the subject disclosure can be performed alone or in combination with other steps or functions of the subject disclosure, as well as from other embodiments or from other steps that have not been described in the subject disclosure. Further, more than or less than all of the features described with respect to an embodiment can also be utilized.

What is claimed is:

1. A virtual assistant device, comprising:
a processing system including a processor; and
a memory that stores executable instructions that, when executed by the processing system, facilitate performance of operations, the operations comprising:
creating a normalized profile for a user of the virtual assistant device, wherein the normalized profile comprises aggregations of behaviors of interaction with virtual assistant devices among cohorts of users having similar characteristics of the user of the virtual assistant device;

identifying an anomaly deviating from the normalized profile over a threshold time period during use of the virtual assistant device; and changing an interface of the virtual assistant device to accommodate the identified anomaly.

2. The virtual assistant device of claim 1, wherein the normalized profile includes metrics for user performance.

3. The virtual assistant device of claim 2, wherein the user performance includes user response time.

4. The virtual assistant device of claim 2, wherein the user performance includes frequency of usage.

5. The virtual assistant device of claim 1, wherein the normalized profile is created among cohorts of people.

6. The virtual assistant device of claim 1, wherein the anomaly is identified through pattern matching.

7. The virtual assistant device of claim 1, wherein the anomaly is an indirect condition.

8. The virtual assistant device of claim 7, wherein the indirect condition is depression, a cognitive degradation or a physical degradation.

9. The virtual assistant device of claim 1, wherein the threshold time period comprises weeks, months or years.

10. The virtual assistant device of claim 1, wherein changing the interface comprises proactively reminding the user to complete a missed task.

11. The virtual assistant device of claim 1, wherein the operations further comprise recommending additional behavioral changes to the user to overcome the identified anomaly.

12. The virtual assistant device of claim 1, wherein the operations further comprise seeking external assistance for the identified anomaly.

13. The virtual assistant device of claim 1, wherein the processing system comprises a plurality of processors operating in a distributed computing environment.

14. A non-transitory, machine-readable medium, comprising executable instructions that, when executed by a processing system including a processor, facilitate performance of operations, the operations comprising:

creating a behavior model for a user of a virtual assistant device, wherein the behavior model comprises aggregations of behaviors of interaction with virtual assistant devices among cohorts of users having similar characteristics of the user of the virtual assistant device;

identifying an anomaly in a behavior of the user that deviates from the behavior model over a threshold time period during use of the virtual assistant device; and changing an interface of the virtual assistant device to accommodate the identified anomaly.

15. The non-transitory, machine-readable medium of claim 14, wherein the operations further comprise recommending behavioral changes to the user to overcome the identified anomaly.

16. The non-transitory, machine-readable medium of claim 14, wherein the operations further comprise coupling the behavior model with cognitive monitoring to identify the anomaly.

17. The non-transitory, machine-readable medium of claim 16, wherein the cognitive monitoring comprises cognitive assessments for reading comprehension, interaction speed, familiarity with a topic or calendar appointments, medicine consumption, or a combination thereof.

18. The non-transitory, machine-readable medium of claim 14, wherein the processing system comprises a plurality of processors operating in a distributed computing environment.

19. A method, comprising:

selecting, by a processing system including a processor, a behavior model for a user of a virtual assistant device, wherein the behavior model comprises aggregations of cognitive behaviors of interaction with virtual assistant devices among cohorts of users having similar characteristics of the user of the virtual assistant device;

identifying, by the processing system, an anomaly in a cognitive behavior of the user that deviates from the behavior model over a threshold time period during use of the virtual assistant device; and adapting, by the processing system, an interface of the virtual assistant device responsive to the identified anomaly.

20. The method of claim 19, comprising: coupling, by the processing system, the behavior model with cognitive monitoring to identify the anomaly.

\* \* \* \* \*